United States Patent [19]

Ordonez et al.

[11] Patent Number: 5,501,987
[45] Date of Patent: Mar. 26, 1996

[54] DUAL ANALYTE IMMUNOASSAY FOR METHAMPHETAMINE AND AMPHETAMINE

[75] Inventors: Kathy P. Ordonez, Hoboken; Salvatore J. Salamone, Stockton, both of N.J.

[73] Assignee: Hoffmann-La Roche Inc., Nutley, N.J.

[21] Appl. No.: 258,125

[22] Filed: Jun. 10, 1994

Related U.S. Application Data

[63] Continuation of Ser. No. 899,196, Jun. 16, 1992, abandoned.
[51] Int. Cl.$^6$ ................... G01N 33/546; G01N 33/577
[52] U.S. Cl. .................. 436/534; 435/7.93; 436/545; 436/546; 436/816
[58] Field of Search .................... 436/534, 545, 436/546, 816; 435/7.93

[56] References Cited

U.S. PATENT DOCUMENTS

| | | | |
|---|---|---|---|
| 3,878,187 | 4/1975 | Schneider et al. | 436/816 |
| 4,329,281 | 5/1982 | Christenson et al. | 436/822 |
| 4,508,830 | 4/1985 | Baker et al. | 436/518 |
| 4,868,132 | 9/1989 | Byrnes et al. | 436/546 |
| 5,101,015 | 3/1992 | Brynes et al. | 436/501 |
| 5,135,863 | 8/1992 | Hu et al. | 436/532 |

FOREIGN PATENT DOCUMENTS

| | | |
|---|---|---|
| 165716 | 12/1985 | European Pat. Off. . |
| 378391 | 1/1989 | European Pat. Off. . |
| 386644 | 3/1990 | European Pat. Off. . |
| 473065 | 8/1991 | European Pat. Off. . |
| WO92/18866 | 4/1992 | WIPO . |

OTHER PUBLICATIONS

American Academy of Forensic Sciences–1992, (K65) "Enantioselective Polyclonal Antibodies for Methamphetamine."

*Primary Examiner*—Mary E. Ceperley
*Attorney, Agent, or Firm*—George M. Gould; William H. Epstein; Dennis P. Tramaloni

[57] ABSTRACT

The present invention provides a novel immunoassay for the detection of multiple analytes such as amphetamine and methamphetamine in a single assay of a biological fluid sample. In this assay, a single labelled binding partner is utilized capable of cross reacting at differing sensitivities to antibodies derived from conjugate derivatives of the different analytes such that the presence of the analytes at selected levels of concentration of the analytes singly or in combination can be detected.

5 Claims, 1 Drawing Sheet

DUAL ANALYTE IMMUNOASSAY FOR METHAMPHETAMINE AND AMPHETAMINE

This is a continuation of application Ser. No. 07/899,196, filed Jun. 16, 1992, now abandoned.

BACKGROUND OF THE INVENTION

The present invention relates to diagnostic immunoassays of biological fluid samples which are utilized to detect more than one analyte at a time. Dual actions assays have been developed in the past, (U.S. Pat. No. 4,329,281, European Patent Application EPO, 165,716 A1, Syva Emit® Monoclonal Assay for Amphetamine/Methamphetamine and Roche Abuscreen® RIA for Amphetamine/Methamphetamine). These assays are configured by using two labels and two or more antibodies or antibody populations that are specific for each label.

SUMMARY OF THE INVENTION

The present invention provides a novel configuration for a multi-analyte immunoassay of a biological fluid sample in which only one labelled binding partner is used which can interact with the combination of antibodies and their corresponding analytes so as to detect the presence of the analytes at selected cutoff levels either alone or in combination. An exemplary assay is provided utilizing methamphetamine and amphetamine antibodies and a single labelled derivative of one of the two analytes, most preferably amphetamine.

DETAILED DESCRIPTION OF THE INVENTION

Figure 1:
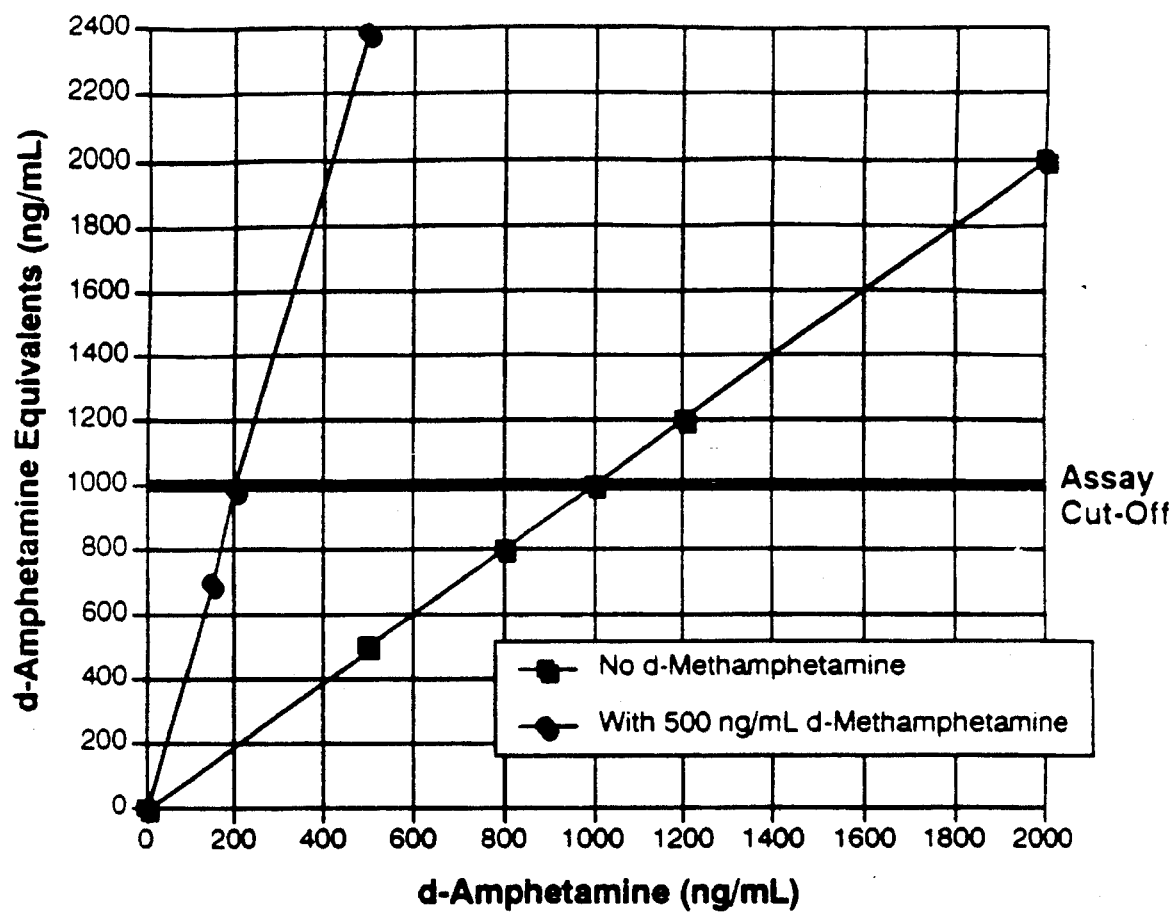
FIG. 1 shows the dose response curves generated for amphetamine alone and amphetamine combined with 500 ng/mL of methamphetamine utilizing a latex agglutination immunoassay in accordance with the present invention.

In the present invention, only one analyte derivative is labelled with a labelling moiety such as a microparticle. This label is constructed such that it has some binding affinity for the antibodies of both analytes of interest. Immunogens derived from the two analytes are then used to generate two antibodies. The immunogens are constructed so as to have certain common features distal from the distinguishing structural features of the analytes of interest. Both antibodies are thus capable of binding the label. However, each antibody is selected so as to only be displaced by its corresponding analyte binding partner, i.e., they are not cross-reactive to the other analytes.

The advantages of the multi-analyte assay of the present invention are that only one labelled binding partner is involved in the configuration rather than the usual pair. This allows for a simplified manufacturing process. Moreover, the specificity of the assay remains high and the assay can provide a standard curve that can be configured to be selectively more sensitive for one analyte over another one. Thus, in a most preferred embodiment of the present invention, the single microparticle labelled derivative is an amphetamine derivative which not only binds with the amphetamine antibody, but also to a lesser degree with methamphetamine antibody. The lesser affinity to methamphetamine allows the cutoffs and the assay sensitivity to be skewed toward the relative amounts for these two drugs in accordance with Federal guidelines for drugs of abuse detection.

This invention can be used in any type of immunoassay format (e.g., turbidometric agglutination assay, radioimmunoassay (RIA), enzyme immunoassay (EIA), fluorescent polarization immunoassay). What is required is that the label structure contain a portion that is homologous to each of the immunogens that are used to generate the corresponding antibodies in order to provide the multi-analyte, multi-antibody interaction with the single label reagent.

The single labelled reagent is constructed such that it contains in the linking arm between the analyte of choice (e.g., amphetamine) and the labelling groups (e.g., chromophore, polyamino tethered microparticle or enzyme, etc.), a substantial portion which is attached to a side of the analyte having common structural features with the other analytes (e.g., the benzene ring of the amphetamines) and distal from the structurally distinct parts thereof, which portion of said linking arm is at least homologous, preferably identical, to the linking arm present in the immunogen used to generate the antibodies to the target analytes.

The remainder of the linking arm may be any reactive spacer-linker group typically used in the art to tether to the labelling moiety chosen such as, e.g., a N-hydroxysuccinimidyl or isothiocyanato group. In the case of binding to a protein portion of a labelling construct one typically preferred approach is a thiourea bond formed with the amino groups of lysine on the protein through an isothiocyanato grouping:

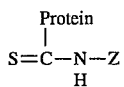

wherein X is an optional additional spacing group such as a divalent alkyl radical, i.e., alkylene, group of one to ten carbon atoms or a phenyl-lower ($C_{1-4}$) alkylene group.

For a methamphetamine/amphetamine latex agglutination immunoassay in accordance with the present invention, the immunologically reactive linking arm should most preferably be attached at the para position of the benzene ring of the amphetamine or methamphetamine. In order to create sufficient common recognition by either analyte's selective antibody for the single analyte label molecule, the linking arm must contain at least one heteroatom functional group. Preferably, the linking arm of the label molecule of the present invention contains a terminal amino group attached to the optional protein bonding tether so as to mimic the amide linkage portion of the immunogen molecules. Thus, the preferred linking arms for the labelled analytic derivative would be represented by the formula

where $X=H_2$, O, S or NH and n=1–6,
and the corresponding linking groups for the immunogens would be —CX—(CH2)m where m may be ±1 or the same as n independently for each immunogen.

Immunogens and antibodies are prepared according to methods known in the art, e.g., U.S. Pat. No. 4,329,281, the disclosure of which is incorporated herein by reference. Formulas 1 and 2 show the preferred amphetamine and methamphetamine immunogens used in the present invention, respectively and Formula 3 shows the preferred amphetamine microparticle label reagent (the amino group shown in the amide bond to the protein is provided by the protein).

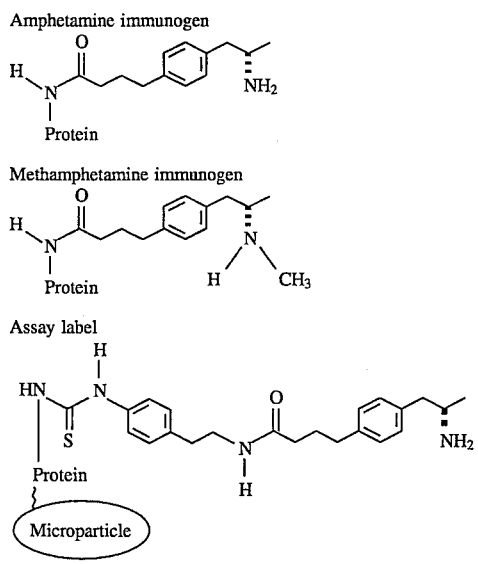

Drug derivatives of analytes such as amphetamine and methamphetamine, are then covalently bound to a carrier protein through a suitable linking arm by methods well known in the art and these conjugates are injected into animals to generate antibody formation. Both polyclonal and monoclonal antibodies may be utilized in the assay of the present invention.

Monoclonal antibodies may be generated according to methods known in the art such as the procedure of Kohler and Milstein, *Nature,* 256, p. 495–497 (1975). The hybridoma cell culture supernatants containing monoclonal antibody are screened by typical ELISA methods using, in the case of the amphetamine/methamphetamine assay, amphetamine-bovine serum albumin (BSA) coated polystyrene microtiter plates for the amphetamine monoclonals and methamphetamine-BSA coated polystyrene microtiter plates for the methamphetamine monoclonals. The amphetamine and methamphetamine derivatives used with the BSA coating are the same as used with the immunogens. The monoclonal antibodies are detected using known methods such as screening with an anti-mouse antibody conjugated to alkaline phosphatase. Final screening of the monoclonals is achieved by the ELISA method followed by analysis in the assay system.

The antibodies that are selected by the ELISA microtiter plate screening show strong binding to the antigen on the plate. In addition to strong binding, antibodies must show good displacement in the presence of: free amphetamine for the amphetamine antibodies and free methamphetamine for the methamphetamine antibodies. Lastly, the antibodies selected have to exhibit low cross-reactivity to free amphetamine-related over-the-counter medications.

In a preferred embodiment of the present invention, microparticle reagents are utilized which incorporate microparticles that are coated with one component of an immunological binding pair which binding pair is diagnostically selective for the substance of interest. The microparticles remain monodispersed. Upon kinetic interaction in the presence of the complementary binding partner the microparticles aggregate resulting in changes of optical density.

For a fluorescent polarization immunoassay, antibodies can be generated according to U.S. Pat. No. 4,868,132 and the corresponding fluorescent labels are synthesized from the same derivatives that are used to form the immunogens. In the case of a RIA, antibodies can be prepared according to U.S. Pat. No. 4,329,281. The corresponding label could be generated by coupling tyramine to the protected activated amphetamine derivative described in U.S. Pat. No. 4,329,281, removing the protecting group and iodinating with $^{125}$I according to U.S. Pat. No. 4,041,076. In the case of an EIA, immunogens could be generated according to U.S. Pat. Nos. 3,878,187 and 4,069,105. The corresponding labels would employ the same derivatives only that they be attached to an enzyme (i.e., Glucose-6-Phosphate Dehydrogenase, Lysozyme) as described in the above patents. In each case the label would contain a linking portion that is homologous to each of the immunogens that are used to generate the corresponding antibodies and the assay development would follow the screening procedures as described above.

The selection procedure involves choosing an amphetamine antibody that can bind amphetamine-BSA sensitized microbead and give greater than 100 milliabsorbance units (mA) displacement with amphetamine in the clinically important range.

In addition the antibodies selected should have a cross-reactivity relative to amphetamine, for amphetamine related analogues of less than 5%.

The selection procedure involved in choosing a methamphetamine antibody is the same as that used in the amphetamine procedure. The only difference is that the derivative used on the microparticle was the methamphetamine derivative and displacement of the antibody was accomplished using methamphetamine.

In both, the amphetamine and methamphetamine cases the derivatives that are used in the immunization and screening processes had structural similarities in the linking arm. This is seen by comparing Formula 1 with Formula 3.

Table 1 exemplifies typical low cross-reactivity of amphetamine and methamphetamine monoclonal antibodies selected in accordance with the present invention utilizing the immunogens of Formulas 1 and 2.

TABLE 1

| COMPOUND | CROSS - REACTIVITY (%) | |
| --- | --- | --- |
| | AMPHETAMINE ANTIBODY | METHAMPHE-TAMINE ANTIBODY |
| l-Methamphetamine | <0.2 | 3.0 |
| d-Amphetamine | 100 | 1.9 |
| d-Methamphetamine | <0.2 | 100 |
| l-Amphetamine | 1.3 | 0.2 |
| Beta-Phenethylamine | 0.5 | <0.1 |
| d-Pseudoephedrine | <0.1 | <0.1 |
| l-Pseudoephedrine | <0.1 | <0.1 |
| d-Ephedrine | <0.1 | <0.1 |
| l-Ephedrine | <0.1 | <0.1 |
| d-Phenylpropanolamine | <0.1 | <0.1 |
| d,l-Phenylpropanolamine | <0.1 | <0.1 |

Once the appropriate antibodies are selected the assay is then configured by determining if the methamphetamine antibody binds the amphetamine label, or if the amphetamine antibody binds the methamphetamine label. In the preferred assay of the present invention the methamphetamine antibody bound the amphetamine label enough to cause aggregation of the microparticles and the amphetamine antibody did not bind to the methamphetamine label enough to cause aggregation of the microparticles.

Therefore, by using microparticles labeled with the amphetamine derivative, a dual action assay can be configured by using both amphetamine and methamphetamine antibodies.

The antibodies are used at a dilution in the assay which allows for the appropriate sensitivity with each of the analytes being determined. In this particular assay the antibody concentrations were adjusted so that methamphetamine containing sample added to the assay by itself would not normally give a positive reading. The curve is based on d-amphetamine standards, (0 to 2000 ng/mL) and positives are achieved only when a sample contains amphetamine alone, or methamphetamine in the presence of a small amount of amphetamine.

This configuration gives a lower false-positive rate by lowering the cross-reactivity of many over-the-counter medications that are related in structure to methamphetamine. FIG. 1 shows the dose response of the assay to amphetamine alone and methamphetamine in the presence of amphetamine. While the dose response to methamphetamine alone is very low the dose response to methamphetamine in presence of amphetamine is very high.

Federal guidelines on drug testing require the presence of amphetamine in methamphetamine containing urine in order to call the sample positive. This is required so that false positive results are minimized and in recognition that methamphetamine is partially metabolized to amphetamine (Basalt, R. C., Disposition of Toxic Drugs and Chemicals in Man, 3$^{rd}$ ed, Year Book Medical Publishers, Inc., 1989).

Surprisingly, the methamphetamine antibody shows significant binding to the amphetamine label of Formula 1, even though the cross-reactivity of the methamphetamine antibody to free amphetamine is low (Table 1).

In fact, there is significant binding of the methamphetamine antibody to the amphetamine label to produce aggregation. Without intending to limit the scope of the present invention to any theoretical mechanism, this binding may be explained by examining the structure of the methamphetamine immunogen (Formula 2) and comparing it with the amphetamine label. While amphetamine itself does not appreciably bind to the methamphetamine antibody added recognition of the side chain that attaches the amphetamine derivative to the protein may be occurring. The specificity of the methamphetamine antibody, however, remains high toward methamphetamine.

The immunoassay reagents and method of the present invention may be usefully employed in any of the agglutinometric formats susceptible to an instrumental method for the measurement of the changes brought about by the agglutination reaction. Both manual as well as automated apparatus testing may be suitably employed for such agglutinometric analysis. Typically, automated instrumentation will operate utilizing a multiplicity of reagent containers or reservoirs from which will be pipetted the appropriate amount of each reagent for addition to the sample. For immunoassays such as the subject agglutination assays, this will usually involve at least two such containers; typically, one for an antibody reagent and the other for the microparticles bound with the corresponding antigenic determinants(s). Additional containers/reservoirs may be present in some instruments containing diluent, buffers and/or other additives for appropriate treatment of the sample.

EXAMPLE 1

PREPARATION OF AMPHETAMINE LABEL

Preparation of (S)-N-(1-methyl-2-phenylethyl)fluoro-acetamide(1):

To a mixture of d-amphetamine sulfate (20.0g, 0.108 mol) in triethylamine (75 mL) that was purged with argon and cooled in an ice bath trifluoroacetic anhydride (31 mL) was added dropwise over 15 min. The reaction was stirred at ambient temperature overnight. The solvents were then evaporated in vacuo and the residue was dissolved in methylene chloride (200 mL), washed with 5% aqueous tartartic acid (3× 250 mL), dried ($Na_2SO_4$), filtered and concentrated in vacuo to yield a yellow oil. The material was crystallized in a hexane ether mixture to yield 14 g of the product. NMR was consistent with predicted structure.

Preparation of (S)-4-[2-methyl-2-[(trifloroacetyl) amino] -ethyl]-p-oxo-benzenebutanoic acid (2):

To a stirred solution of (1), (12.0 g, 0.05 mol) in methylene chloride (210 mL) under argon, succinic anhydride (8.0 g, 0.08 mol) was added. The reaction was cooled in an ice bath and then treated with aluminum chloride (28.0 g, 0.21 mol), portionwise over 5 min. The reaction was stirred at 0°–5° for 2 h and then at room temperature overnight. Hydrochloric acid (3N, 120 mL) was then slowly added and then solution was stirred for an additional one hour. The methylene chloride was removed in vacuo and the aqueous layer was extracted with ethyl acetate. The organic layer was dried ($Na_2SO_4$), filtered and the solvents evaporated to yield a tan residue which upon trituration with ether gave 10.5 g of product. IR, NMR and mass spec. were all consistent with posited structure.

Preparation of (S)-4-[2-methyl-2-[(trifloroacetyl)amino] ethylbenzenebutanoic acid (3):

A mixture of 2 (9.2 g, 0.027 mol), and 10% palladium on charcoal (4.0 g) in acetic acid (400 mL) was hydrogenated at 50 psi for 24 h. The catalyst was filtered off, the filtrate was concentrated in vacuo and the residue was triturated with ether to yield 7.0 g of a white product. IR and NMR spectra and mass spec. were in agreement with structure.

Preparation of (S)-N-[2-{4-{4-{(2,5-Dioxo-1-pyrrolidinyl)-oxy]4 -oxo=butyl]phenyl]-1-methyl-ethyl]-2-trifloro-acetamide (4):

To a stirred solution of 3 (5.4 g, 0.019 mol) in methylene chlorie (150 mL), tetrahydrofuran (150 mL and dimethylforamide (50 mL), N-hydroxysuccinimide (2.7 g, 0.023 mol) and 1-(3-dimethylaminopropyl)-3-ethyl carbodiimide hydrochloride (6.0 g, 0.031 mol) was added. The reaction was stirred at room temperature overnight, and then was concentrated in vacuo. The resulting residue was dissolved in methylene chloride, filtered and purified by silica gel chromatography (7% ethermethylene chloride as eluent) to give a yellow oil which crystallized in a ether to yield 3.7 g of a white product. IR, NMR and MS were consistent with structure.

Preparation of (S)-N-(4-Isothiocyanatophenyl)ethyl)-4-4-(2-(trifluoroacetamido)propyl)benzenebutamide:

To a solution of the N-hydroxysuccinimide derivative, (4) (200 mg, 0.48 mmole) in 8 mL of $CH_2Cl_2$ is added p-aminophenethyl amine (65.7 mg, 0.48 mmole) and 0.5 mL of pyridine. The reaction mixture is stirred for 24 h and $CH_2Cl_2$ is then removed under reduced pressure to give beige solids. The solids are placed on preparative silica gel plates (2.0 mm thickness) and develop this mixture of $CH_2Cl_2$/MeOH (95:5). A desired band is isolated, the silica gel is extracted several times with absolute ethyl alcohol through a buchner funnel, and the solvent is removed under reduced pressure to give beige solids, 125 mg (60%). Rf:0.35(95:5 $CH_2Cl_2$/ MeOH).

The aminophenethyl amide adduct above (94 mg. 0.22 mmole) is dissolved in 3 mL of THF, 3 mL of $H_2O$, and 1 mL of saturated $NaHCO_3$. After cooling under an ice-bath for 15 minutes, thiophosgene (33 mg, 0.28 mmole) is added to the mixture. This is stirred for an additional 30 minutes and a dilute HCl(0.1N) is added until pH of the solution reaches 3.0. THF is then removed under reduced pressure. The aqueous solution is extracted 3x with CHCl$_3$, the combined organic layer is washed with H$_2$O, and dry with anhydrous Na$_2$SO$_4$. Removal of the solvent gives beige solids 63 mg (60%). Rf=0.59 (95:5 CH$_2$Cl$_2$/MeOH). NMR was consistent with posited structure.

Preparation of Amphetamine-BSA Conjugate

Materials:

Bovine Serum Albumin (BSA), Fraction V, Reagent Grade, amphetamine derivative, Molecular Weight 477.55 mg/mM, Dimethyl Sulfoxide (DMSO), 50 mM potassium phosphate buffer pH=8.0 (KPi buffer), 50 mM sodium carbonate buffer (pH 11.3), stock solution of amphetamine (5 mg/mL): 5 mg of amphetamine derivative in 1.0 mL of DMSO, Dialysis membrane 25,000 MWCO.

Method:

The BSA to be conjugated is prepared by dissolving 69 mg in 1.24 mL of phosphate buffer (pH 8). Once the protein has completely dissolved chill the solution in an ice bath. While stirring, DMSO (1.51 mL) is added dropwise to the protein solution which is then allowed to come to room temperature. At this point the stock solution of amphetamine derivative may be freshly prepared (see above). The stock solution (0.10 mL) of amphetamine derivative is added to the protein in DMSO/buffer. The reaction continues to stir overnight at room temperature. The conjugate is initially dialyzed at room temperature against 15 mL DMSO diluted with 35 mL of KPi (pH 7.5) buffer and then against 5 mL of DMSO diluted with 45 mL of KPi buffer. Dialysis then continues at 4_C against KPi buffer. Conjugate recovered is evaluated for protein concentration at 280 nm.

The protein conjugate is then diluted to a 12.0 mg/mL concentration in KPi (pH 7.5) buffer and dialyzed (eight times volume, nine times over a three day period) in the carbonate buffer (pH 11.3). The conjugate is then dialyzed against a second carbonate buffer (eight times volume, six times over a three day period).

Preparation of sensitized microparticle containing the amphetamine BSA conjugate:

Materials:

Carboxylated polystyrene microparticles (diameter 0.1 to 0.13 um manufactured by Seradyn, Inc.), N, N-Dimethylformamide (DMF), 1-Hydroxybenzotriazole (NHB;H$_2$O), 1-Cyclohexyl-3(2-Morpholinoethyl) carbodiimide metho-p-toluene sulfonate (CMC), Triton X-100, amphetamine-BSA conjugate, 50 mM Sodium Bicarbonate pH 8.6, BSA Fraction V Reagent Grade, buffer of 10 mM KPi, pH 7.5 0.1% sodium azide, and 0.1% triton X-100 (microparticle storage buffer).

Methods:

The carboxylated microparticles (8.0 mL of 10% solids), as supplied by the manufacturer is washed to exchange the detergent. Triton X-100 at 0.1% in deionized water is used for a total dilution of greater than 1:1,000,000 by volume. The washed latex in 0.1% Triton X-100 is adjusted to 3% solids in 0.1% Triton X-100 from a standard curve of latex concentration at 500 nm.

A stock solution of NHB is prepared by dissolving 31 mg NHB in 0.5 mL of DMF to which deionized water (0.75 mL) is added (25 mg NHB/mL). While rapidly stirring the prepared microparticle solution (20 mL) at room temperature the NHB solution (1.25 mL) is added rapidly dropwise. The solution is stirred for ten minutes during which the stock solution of CMC is made up.

The stock solution of CMC is prepared by dissolving 86 mg CMC in 1.73 mL (50 mg CMC/mL) of deionized water. With rapid stirring 1.73 mL are added rapidly dropwise to the microparticle solution prepared above. Following this addition the reaction is stirred for three hours at room temperature. The excess activating reagents are removed by again washing the microparticle preparation with 0.1% Triton X-100 for a total dilution of 1:1,000,000. The microparticles are adjusted to 2% solids by comparison to a standard curve of microparticle concentration at 500 nm.

The BSA conjugate prepared previously is used in the following way to sensitize the microparticles. The conjugate (15.6 mg) is diluted to 5 mg conjugate BSA/mL with 50 mM sodium bicarbonate pH 8.5. Bovine Serum Albumin Fraction V, reagent grade (109.4 mg) is dissolved in 21.88 mL of sodium bicarbonate (5 mg BSA/mL) pH 8.5. The BSA (21.88 mL) and BSA conjugate (3.12 mL) solutions are then combined for 25 mL total volume of 5 mg BSA/mL. While vigorously mixing the protein solution, the activated microparticles (25 mL) are added rapidly. The reaction is mixed overnight. Unbound BSA conjugate is then removed by extensive washing. The final latex suspension is diluted with 10 mM KPi, 0.1% Triton-X-100, 0.1% sodium azide, pH 7.5 and 10 mM KPi, 0.1% sodium azide, pH 7.5 for a final microparticle reagent at 0.7% solids in 10 mM KPi, 0.10% Triton-X-100, 0.1% sodium azide pH 7.5. The percent solids of the microparticles is determined by comparison to a standard curve of microparticle concentration at 500 nm.

EXAMPLE 2

AMPHETAMINE/METHAMPHETAMINE ASSAY

Preparation of Antisera Reagent for Test:

Mouse monoclonal antibodies selective against amphetamine and methamphetamine were generated from immunogens prepared in accordance with the procedures of Examples 6, 13 and 14 of U.S. Patent No. 4,329,281 utilizing bovine thyroglobulin as the carrier proteins. The monoclonals were then diluted appropriately in an aqueous solution at pH 7.5:

1. 0.05M Potassium Phosphate
2. 0.01% Bovine Serum Albumin
3. 0.5% Sodium Chloride
4. 0.1% Sodium Azide The proportion and concentration of the amphetamine and methamphetamine antibodies are adjusted so that an approximate span of 200 milliabsorbance (mA) units is achieved between 0 and 1000 ng/mL of d-amphetamine and that an approximate span of 45 mA is achieved between 1000 and 2000 ng/mL. In addition, the 200 ng/mL damphetamine with 500 ng/mL d-methamphetamine standard gives a reading similar to the 1000 ng/mL d-amphetamine standard.

A series of titres are then run against dilutions of the amphetamine and methamphetamine antibodies in accordance with the following grid.

| METHAMPHETAMINE | AMPHETAMINE TITER | | | | |
|---|---|---|---|---|---|
| TITER | 1:100 | 1:125 | 1:150 | 1:175 | 1:200 |
| 1:100 | | | | | |
| 1:125 | | | | | |
| 1:150 | | | | | |
| 1:175 | | | | | |
| 1:200 | | | | | |

The concentrations thus identified are "fine tuned" by testing small changes of concentration around a particular point in order to achieve the cut-off sensitivities desired (see FIG. 1).

Preparation of Sample Diluent for Test:
The reaction buffer is an aqueous solution at pH.7.0
1. 0.05M PIPES [1,4-piperazinebis(ethanesulfonic acid) and disodium salt.]
2. 5% PVP [polyvinylpyrrolidone]360
3. 2.0% Sodium Chloride
4. 0.1% Sodium Azide
5. 0.025% Foamaster, FLD Assay for amphetamine abuse:

The diagnostic screening assay is performed on the ROCHE COBAS MIRA. Standards are prepared by the addition d-amphetamine to drug free normal human urine containing 0.1% sodium azide. The clinical analyzer pipettes the onboard reagents and samples into one cuvette where the competitive agglomeration reaction occurs and measurement of the turbidity is made. Reagent transfer is accomplished in two stages. Stage 1: 20 microliters of urine sample are pipetted with 75 uL of sample diluent into the cuvette, followed immediately by 100 uL of the antibody reagent and mixing. The initial spectrophotometric reading is taken. Twenty-five seconds later, Stage 2: 30 uL of microparticle reagent with 65 uL of water are transferred into the cuvette and the reaction is mixed. About 150 seconds after stage 2, a final measurement of the turbidity is made. The overall change in turbidity in the reaction is compared to a calibration curve, and results reported in ng/mL.

These assay components and antibody titer give a standard curve with desired performance characteristics around the NIDA cut-off of 1000 ng/mL d-amphetamine and 200 ng/mL d-amphetamine with 500 ng/mL d-methamphetamine (FIG. 1). In addition, Table 2 shows the cross-reactivity that this assay has with some of the amphetamine related drugs. The following structurally related compounds were tested for cross-reactivity. The compounds were prepared in pooled human urine. The results are expressed as the concentration of drug which produces a response equivalent to 1000 ng/mL d-Amphetamine.

TABLE 2

| Compound | Approximate ng/mL Equivalent to 1000 ng/mL Amphetamine ng/mL | % Cross-Reactivity |
|---|---|---|
| Methylenedioxy-amphetamine (MDA) | 2457 | 40.70 |
| B-Phenylethylamine | 52493 | 1.90 |
| p-OH Amphetamine | 56818 | 1.76 |
| L-Phenylpropanolamine | 79428 | 1.26 |
| D,L-Phenylpropanolamine | 126742 | 0.79 |
| D-Methamphetamine | 219298 | 0.46 |
| Propylhexidrine | 245098 | 0.41 |
| L-Amphetamine | 246305 | 0.40 |
| Tyramine | 246305 | 0.40 |
| p-OH Methamphetamine | 303951 | 0.33 |
| L-Methamphetamine | 444444 | 0.23 |
| D-Phenylpropanolamine | 438596 | 0.23 |
| Methylenedioxy-methamphetamine (MDMA) | 427350 | 0.23 |

We claim:

1. In a dual analyte immunoassay for the detection of amphetamine and methamphetamine in a sample, wherein to the sample is added an antibody selective for amphetamine and an antibody selective for methamphetamine, and whereby the presence of amphetamine and/or methamphetamine is determined by measuring the amount of a labelled reagent which remains bound or unbound to such antibodies as a result of competitive displacement by an analyte which may be present in such sample, the improvement comprising utilizing as the labelled reagent an amphetamine of the formula:

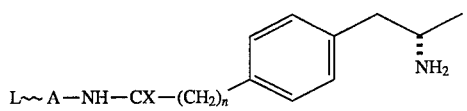

wherein L is a detectable labelling moiety, A is a linkage group capable of physically or chemically binding to L, X is H2, O, S or NH, and n=1–6;

the antibody selective for amphetamine is generated by an immunogen of the formula:

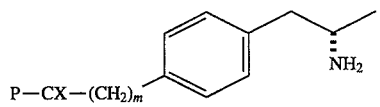

and the antibody selective for methamphetamine is generated from an immunogen of the formula:

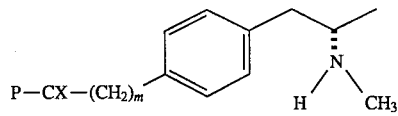

where m and m' are ±1 or the same as n independently for the methamphetamine and amphetamine immunogens, and P is a poly (amino acid) having reactive amine groups.

2. The improved immunoassay of claim 1 wherein the antibody is a monoclonal antibody.

3. The improved immunoassay of claim 1 wherein L is a microparticle and the assay format is agglutinometric.

4. The immunoassay of claim 1 wherein the amphetamine immunogen, methamphetamine immunogen and labelled derivative are of the formulas 1, 2 and 3:

Amphetamine immunogen

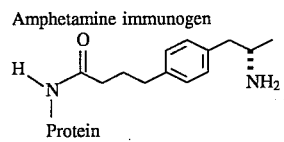

1

Methamphetamine immunogen

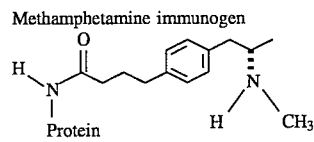

2

Assay label

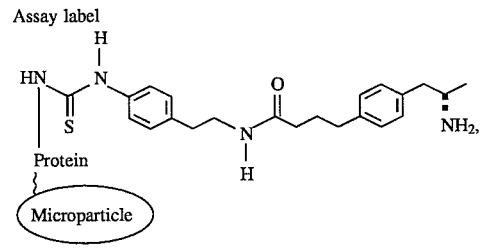

3

5. The immunoassay of claim 1 wherein L is a microparticle and A is an isothiocyanate activated protein linkage of the formula:

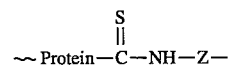

and Z is $C_1$ alkylene or phenyl lower ($C_{1-4}$) alkylene.

* * * * *

UNITED STATES PATENT AND TRADEMARK OFFICE
CERTIFICATE OF CORRECTION

PATENT NO. : 5,501,987
DATED : March 26, 1996
INVENTOR(S) : Kathy P. Ordonez and Salvatore J. Salamone It is certified that error appears in the above-indentified patent and that said Letters Patent is hereby corrected as shown below:

In Column 10, Claim 5, line 65, delete "$C_1$" and insert therefor -- $C_{1-10}$ --.

Signed and Sealed this

Sixth Day of August, 1996

Attest:

BRUCE LEHMAN

Attesting Officer

Commissioner of Patents and Trademarks